United States Patent [19]

Dupont

[11] Patent Number: 4,997,092

[45] Date of Patent: Mar. 5, 1991

[54] STERILE SEALED PACKAGING ENVELOPE

[76] Inventor: George Z. Dupont, 602 Dover Dr., Ste. 3, Newport Beach, Calif. 92807

[21] Appl. No.: 483,678

[22] Filed: Feb. 23, 1990

Related U.S. Application Data

[63] Continuation-in-part of Ser. No. 415,621, Oct. 2, 1989, abandoned.

[51] Int. Cl.⁵ .................... B43M 7/00; B65D 75/58; B65D 77/30
[52] U.S. Cl. .................................. 206/632; 206/813
[58] Field of Search .................... 206/632, 631, 813

[56] References Cited

U.S. PATENT DOCUMENTS

| | | | |
|---|---|---|---|
| 2,172,455 | 9/1939 | Samuel | 206/632 X |
| 2,949,370 | 8/1960 | Hughes | 206/632 |
| 3,412,771 | 11/1968 | Ralph | 206/632 |
| 3,738,566 | 6/1973 | Foster | 206/632 |
| 3,835,990 | 9/1974 | Sagi et al. | 206/632 X |
| 3,917,160 | 11/1975 | Olerud | 206/632 |
| 3,926,311 | 12/1975 | Laske | 206/632 |
| 3,967,729 | 7/1976 | Tanner, II | 206/632 X |
| 3,995,739 | 12/1976 | Tasch et al. | 206/632 |

FOREIGN PATENT DOCUMENTS

| | | | |
|---|---|---|---|
| 105434 | 6/1963 | Netherlands | 206/632 |

*Primary Examiner*—William I. Price
*Attorney, Agent, or Firm*—Francis X. LoJacono

[57] ABSTRACT

The present invention discloses an adhesively sealed, sterile, packaging apparatus that includes a sterile envelope having a sterile compartment to receive all or part of a sterile article therein and wherein a second embodiment is included having two half sections that are adhesively sealed and joined together so as to allow a sterile article to be encapsulated within the sterile envelope defined thereby. Each embodiment provides a sterile enviroment therein and allows the envelope or sections thereof to be readily pulled apart without contaminating the sterile article.

1 Claim, 2 Drawing Sheets

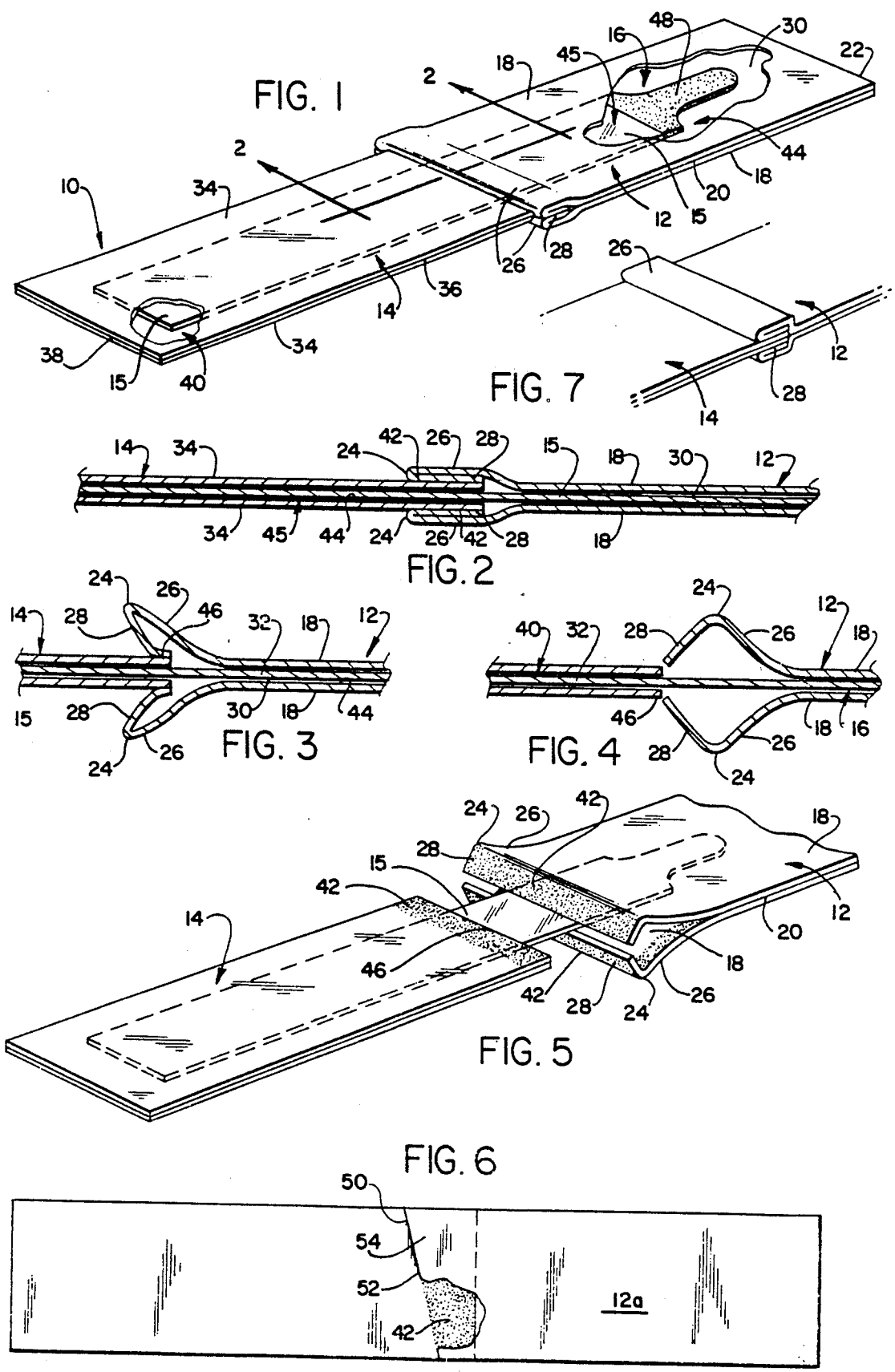

4,997,092

STERILE SEALED PACKAGING ENVELOPE

This application is a Continuation-In-Part of pending application Ser. No. 07/415,621, by George Z. Dupont, filed on Oct. 2, 1989, having the above title and now abandoned.

BACKGROUND OF THE INVENTION

1. Field of the Invention

The present invention relates generally to a packaging or container means and more particularly to an adhesively sealed, sterile, packaging apparatus defined by a two-piece sterile envelope wherein the two pieces are adhesively sealed together so as to allow all or part of the sterile article or object to be encapsulated therein. This arrangement of the two sections which are adhesively sealed together in a sterile manner establishes a completely sterile environment therein for whatever device, instrument or object that may be encapsulated therein.

2. Description of the Prior Art

As is well known in the art, various problems and difficulties are encountered in providing a sterile container, package, or envelope that, when opened, prevents the sterile article from being exposed to contamination by mishandling of either the package or the article itself.

Many types of sterile containers and packages are known and are in use in the medical field. These devices are defined by various configurations and include different methods or means of separation so as to accommodate particular sterile instruments or articles. However, the arrangements and structures of these known packaging members very often do not provide the proper sterile condition or environment that allows for the proper removal of an enclosed sterile article without contamination thereof. Once fully open, many sterile packages do not provide a condition whereby the sterile article can be removed without being contaminated inadvertently. This is particularly true when a sterile article or object is encapsulated within a sealed sterile envelope and must be removed during surgery.

There have been several attempts in the past to provide sterile packaging for various types of sterile products that fall within the scope of the present invention. However, it has been well established that few sterile packages have been designed to overcome the difficulties in maintaining a sterile environment for a sterile article once a package is opened and the article is ready to be removed therefrom so as to be handled by the doctor or the doctor's assistant. Many envelope-type packages are so designed that the enclosed sterile object or instrument is readily exposed to contamination as the object is removed completely from the sterile environment of the package or envelope.

As some examples of adhesively sealed packages and containers, the following patents, which were obtained during a search on the subject matter of the present invention, are of interest.

In U.S. Pat. No. 2,172,455 there is disclosed a bandage package which covers both sides of an adhesive bandage or dressing, which has been folded together, with rubber or with fabric treated or impregnated with rubber solution only.

U.S. Pat. No. 2,889,039 to Schladermundt et al discloses an adhesive bandage that is enclosed in a pair of wrapper sheets. The wrapper sheets may be two separate sheets or may be integrally connected as a single piece and folded over, which forms an envelope. Midway of the wrapper there is provided a tear region which is defined by a weakened area or seam whereby the envelope can be pulled apart.

U.S. Pat. No. 3,025,957 to Wall discloses a packaged surgical drape unit wherein an adhesive-coated surgical drape is enclosed in an envelope which functions both as a sterile protector for the sheet and as a removable liner for the adhesive.

U.S. Pat. No. 3,344,915 to Rawlings relates to an improvement in packages for flat articles such as surgical supplies and to the method of making same. Again, this device is formed from a pair of flat pieces of material.

In U.S. Pat. No. 3,604,616 to Grief there is disclosed a sterilizable envelope for retaining articles before, during and after sterilization. One wall of the envelope is made of an opaque material, such as paper, and the other wall is a transparent material, such as plastic film, these materials being sealed together around the periphery of the envelope and pulled apart to expose the enclosed sterile article.

U.S. Pat. No. 3,899,077 to Spiegelberg is a strip package for an adhesive bandage which is formed from a carrier having a central pad and adhesive surface zones on each side covered by a removable protective foil. The bandage is inserted in an eveloping casing open at one end so that one edge of the bandage projects therefrom.

U.S. Pat. No. 4,235,337 to Dotta discloses a rapidly opening sealed package for wound dressing adhesive tape comprising an adhesive support carrying a wound dressing pad covered endwise by a pair of protective films attached to a pair of outer sheaths so that by pulling the outer sheaths apart the protecting films will move therewith to separate centrally and uncover the wound dressing pad.

A rapidly opening sealed package for wound dressing adhesive tape is disclosed in another U.S. Pat. No. 4,418,822, to Dotta which comprises an adhesive support carrying a wound dressing pad covered endwise by a pair of protective films attached to a pair of outer sheaths so that by pulling the outer sheaths apart the protective films will move therewith to separate centrally and uncover the wound dressing pad. An adhesive layer is applied adjacent said wound dressing pad between said protective films and said outer sheaths. In this manner a material of poor adhesive power such as siliconated paper may be used for the protective films.

Another adhesive tape securing system and method of using same is disclosed in U.S. Pat. No. 4,605,577 to Bowytz. This is in particular a system for packaging precut lengths of double-faced adhesive tape and a method of applying the tape.

SUMMARY AND OBJECTS OF THE INVENTION

The present invention comprises a novel arrangement for encapsulating a sterile medical instrument or object therein. One embodiment of the invention is defined by a sterile envelope having two adhesive or suitably bonded sealed sections that form a sealed sterile chamber. The section members are arranged with each having its own compartment wherein an outer section receives the oppositely positioned inner section therein. A sterile adhesive bonding material is disposed along the open ends of each section to provide a means to secure the two sections together so as to define the single elongated sterile chamber. Various types of medical devices are readily suitable for this type of sterile packaging which allows one to remove a sterile medical instrument or object without contamination. For simplicity, the word "article" will hereinafter represent various medical devices that are suitable for used in conjunction with the present invention.

A second embodiment of the present invention employs a single sterile envelope having a sealable open end wherein only the sterile portion of a medical instrument or object is sealed within the sterile compartment of the envelope.

Thus, the present invention has for an important object a provision to establish a simple envelope that is readily sealed in a sterile manner, whereby sterile medical articles and or instruments may be stored in the sterile chamber thereof and readily removed therefrom when needed by the doctor for treating or operating on a patient, with a minimal risk of contamination to the article.

It is another object of the invention to provide a means of forming a removable, sterile, packaging envelope which includes two sections that can be readily separated by holding the outer end of each section of the envelope and pulling them apart whereby the outer section that covers the article is the first to be removed, and wherein the second or inner section of the two-piece envelope remains to protect the article from contamination while it is being held.

A further object of the present invention is to provide a device of this character wherein medical techniques requiring application of sterile articles (cotton-tipped applicators, chemically tinted paper strips, etc.) are made easier since the doctor or technician may grasp the inner section of the envelope, exposing the sterile tip portion of the article, whereby the article may be utilized in the prescribed manner without contamination.

Still a further object of the invention is to provide an envelope that is defined by a single sterile compartment wherein only the sterile tip portion of a medical article is required to protected. That is, the open end of the envelope is removably attached to the article whereby the sterile portion thereof is protected until the envelope is removed from the article by grasping with one hand the exposed portion of the article and grasping the end of the envelope, and then pulling them apart whereby the envelope will readily peel away from the sterile end of the article.

The characteristics and advantages of the invention are further sufficiently referred to in connection with the accompanying drawings, which represent two embodiments. Other variations may be made without departing from the principles disclosed and I contemplate the employment of any structures, arrangements of modes of operation that are properly within the scope of the appended claims.

BRIEF DESCRIPTION OF THE DRAWING FIGURES

With the above and related objects in view, the invention consists in the details of construction and combination of parts, as will be more fully understood from the following description, when read in conjunction with the accompanying drawings and numbered parts, in which:

FIG. 1 is a perspective view of the present invention showing the adhesive-secured sterile envelope sealed with a sterile article encapsulated therein;

FIG. 2 is an enlarged cross-sectional view taken substantially along line 2—2 of FIG. 1, showing the overlapping of the open end of the two half sections of the envelope and the sealing therebetween;

FIG. 3 is a view similar to that of FIG. 2, but showing the sections being pulled apart at their adhesive bonding point;

FIG. 4 is another cross-sectional view thereof, showing the complete separation of the two sections;

FIG. 5 is a pictorial view of the present invention, showing the separation of the outer section from the article, the article being still positioned in the compartment of the inner section.

FIG. 6 is a top plan view of an alternative arrangement of the present invention.

FIG. 7 is partial pictorial view of another alternative arrangement of the invention.

DETAILED DESCRIPTION OF THE INVENTION

Figure 8:
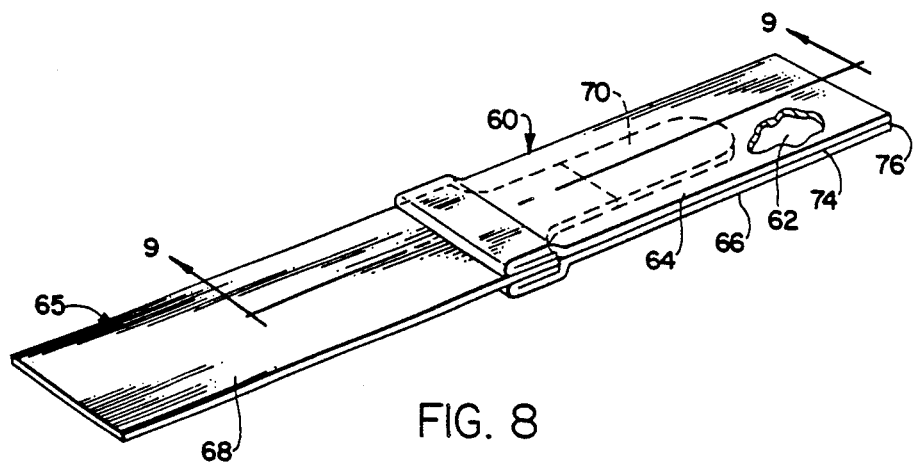
FIG. 8 is a perspective view of an alternative arrangement of the invention wherein only a single envelope is provided to cover the sterile portion of an article.

Referring more particularly to FIG. 1, there is shown a sterile packaging envelope, generally indicated at 10, which is formed by two section members, one being referred to as the outer section 12 and the other being referred to as the inner section 14. When the sections are secured together, they define an elongated compartment 16 in which a sterile article or object 15 is encapsulated under a sealed sterile environment. Section member 12 is formed by a pair of cover sheets 18 which are fixedly secured along the peripheral side edges 20 and the distal end 22 thereof. The opposite end 24 thereof is provided with an open end that is formed having folded transverse overlapping edges 24 defined by an outer lip 26 and an inner lip 28, lip member 28 being folded inwardly under outer lip 26, as shown in FIGS. 1 through 5. Edges 20 and 22 are secured by any suitable means, but preferably by means of a sterile adhesive material. Accordingly, outer section 12 defines a sterile chamber 30 adapted to receive and cover a portion of an article, as indicated at 15. The inner section member 14 is also formed by a pair of flat sheet members 34 which can be made from any suitable material, such as sterile paper or plastic which would correspond to the material comprising the outer section 12. Section 14 is thus defined by sheets 34 which are sealed along three edges that include side edges 36 and the edge of distal end 38, the opposite end thereof being formed as an open end so as to provide access to the interior chamber 40 defined by the arrangement of the superposed sheets 34. It is to be noted that outer section 12 is formed having a larger width than that of the inner section 14, whereby the proximal end of inner section 14 will readily fit within the open end of outer section 12, the two sections being secured together by an adhesive bonding as indicated at 42, better seen in FIG. 5. The adhesive material may be located on lip member 28 or on the outer surface of the open end of sheets 34, or both, as illustrated in FIG. 5.

However, there is shown in FIG. 7 an alternative arrangement wherein both the outer section and the inner section are formed having the same widths.

Accordingly, when the two sections 12 and 14 are secured together in a sealed configuration as illustrated in FIGS. 1 and 2, an elongated compartment 44 is eatablished thereby. This compartment provides the necessary sterile environment that is required by a sterile article enclosed therein. Again, many types of medical devices are suitable for use with this novel sterile packaging envelope. However, the present invention 10 is shown (example) as having a chemically tinted, paper-strip applicator 45 enclosed within compartment 44. For example, if an eye doctor requires the use of the paper-strip medical applicator 45, the envelope is easily opened by pulling each free end of sections 12 and 14 in opposite directions, whereby the two sections 12 and 14 separate. That is, outer section 12 will peel away from inner section 14, as shown in FIGS. 3 and 4. More particularly, FIG. 3 illustrates how sheets 12, when pulled, will cause both lip members 28 and 26 to lift and peel, whereby adhesive covered lip 26 is readily separated from the proximal end 46 of inner section 14. It can be readily understood that the arrangement of the sections together with their central sealing allows for the two sections to be separated without contaminating the sterile article stored therein, even if the outer surface of the package is not clean or sterile. It should be noted that both sides of lips 28 are still sterile when they are peeled from sheets 34 of section 14. As long as inner section 14 remains in place, contact by the user is prevented and thus the article will remain sterile for proper application of the sterile treated end 48.

Thus, it can be readily seen that other types of sterile articles may be enclosed as well, such as cotton-tipped applicators, clamps, etc. Only the unsterile outer surface of the inner cover 14 is grasped by the doctor or technician, thereby protecting the exposed sterile portion of the sterile object 15.

Referring now to the alternative form of the present invention as illustrated in FIG. 6, there is shown that the leading edge 50 of the open end of the outer section 12a is arranged with an inclined or angulated edge 52. This arrangement allows the enlarged sealed edge portion 54 to be peeled first, thereby making the separation of the two sections easier to accomplish without too much effort. Thus, the package may be opened more easily and quickly, especially if the surgery is done under subdued light, as often is the case during eye surgery. Further, with this method of opening the envelope, a firm grip on the still-covered portion the sterile article provides a means for transfer of delicate surgical instruments without harm.

Figure 9:
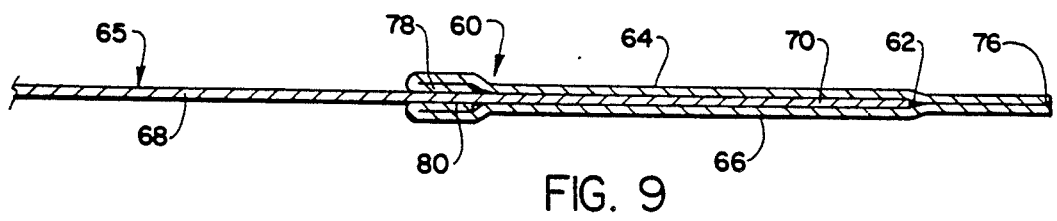
FIG. 9 is an enlarged cross-sectional view taken substantially along line 9—9 of FIG. 8.
Figure 10:
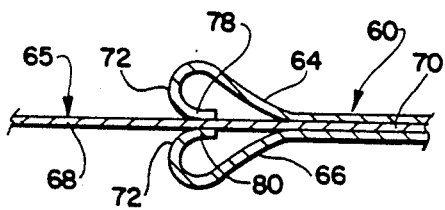
FIG. 10 is a view similar to FIG. 9 showing the envelope being peeled from the sterile end of the article.

Referring now to another embodiment of the invention which is illustrated in FIGS. 8 through 12, there is disclosed an envelope, generally indicated at 60, that is formed having a sterile compartment 62 defined by a first and second sheet 64 and 66, respectively. As with the above described embodiments, sheets 64 and 66 are secured in a suitable manner that will allow for easy and sterile removal of a sterile article or object 65 from the envelope. Article 65 is shown as a strip member having a free exposed end member 68 and a sterile end 70. It thus should be noted that in this arrangement the sterile end 70 is the only part of article 65 that is protected from an unsterile environment. Accordingly, the sterile end 70 is protected by being encapsulated within the sterile compartment 62 os enveloped 60. Suitable adhesive 72 is located along the inner longitudinal edges 74 and transverse edge 76 of sheets 64 and 66. However, an oppositely disposed open end of the envelope is defined by transverse edges 78 and 80 arranged to be sealed and secured to article 65 so as to cover and encapsulate sterile end 70 of article 65, as illustrated in FIGS. 8, 9 and 10. This shows the outer surfaces of edges 78 and 80 as being coated with adhesive 72 and thus sealable about article 65. In FIGS. 8 and 9 edges 78 and 80 are folded back and under with the outer adhesive sides being secured to the respective surfaces of article 65. Sterile end 70 is at this time securely sealed within compartment 62 and free from foreign contamination. It should also be noted however that a sealing means can be located on the article, such as indicated at 71 in FIG. 12.

In FIG. 10, article 65 is shown as being separated from the protective envelope 60. This is accomplished by grasping the exposed free end 68 of article 65 with one hand and with the other hand grasping the far end of envelope 60, and pulling each end in opposite longitudinal directions. Edges 78 and 80 will peel back in a rolling action so as not to contaminate the sterile portion 70.

Figure 11:
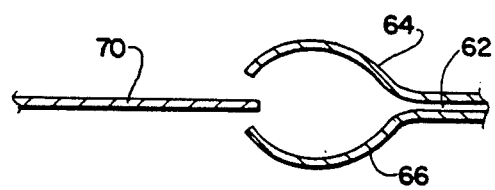
FIG. 11 is a cross-sectional view thereof, showing the envelope completely separated from the article.
Figure 12:
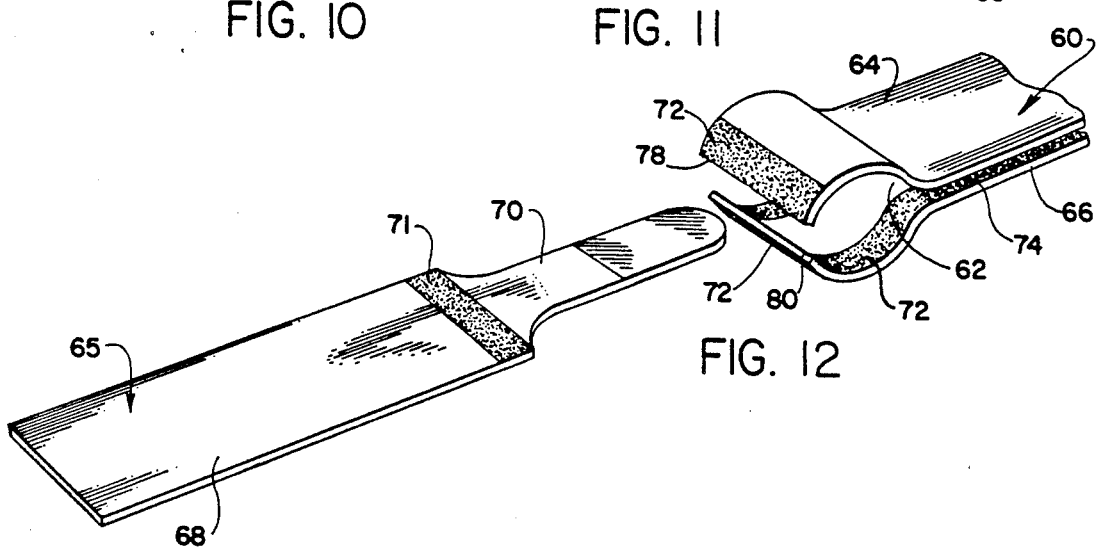
FIG. 12 is a pictorial presentation of the view of shown in FIG. 11.

FIGS. 11 and 12 show article 65 and envelope 60 totally separated from each other.

It may thus be seen that the objects of the present invention set forth herein, as well as those made apparent from the foregoing description, are efficiently attained. While preferred embodiments of the invention have been set forth for purpose of disclosure, modifications of the disclosed embodiments of the invention as well as other embodiments thereof may occur to those skilled in the art. Accordingly, the appended claims are intended to cover all embodiments which do not depart from the spirit and scope of the invention.

What I claim is:

1. A sterile packaging envelope in combination with a sterile article partially enclosed and sealed therein, said combination comprising:

a sterile sealable envelope having a sealable open end in which a sterile compartment is defined thereby;

a sterile article having a selective portion thereof sealed and encapsulated in said sterile compartment;

said open end of said envelope being defined by a pair of folded lip members positioned for engagement with said article; and means for securing said lip members to said sterile article whereby at least a portion of said sterile article is sealed in the sterile environment of said sterile compartment, wherein said securing means comprises adhesive means positioned between said folded lip members and said article, and wherein said adhesive means is positioned on said sterile article for sealing engagement with said lip members of said envelope, whereby said lip members are lifted and peeled upwardly and downwardly as said envelope is pulled from said article.

* * * * *